(12) United States Patent
Christensen (10) Patent No.: US 8,329,455 B2
(45) Date of Patent: Dec. 11, 2012

(54) SYSTEMS AND METHODS FOR DIGESTION OF SOLID WASTE

(75) Inventor: Christian B. Christensen, Hedehusene (DK)

(73) Assignee: Aikan North America, Inc., Atlanta, GA (US)

( * ) Notice: Subject to any disclaimer, the term of this patent is extended or adjusted under 35 U.S.C. 154(b) by 0 days.

(21) Appl. No.: 13/226,006

(22) Filed: Sep. 6, 2011

(65) Prior Publication Data
US 2012/0015430 A1    Jan. 19, 2012

Related U.S. Application Data

(60) Provisional application No. 61/505,696, filed on Jul. 8, 2011.

(51) Int. Cl.
*C12M 1/00* (2006.01)

(52) U.S. Cl. ............ 435/290.4; 435/290.1; 435/290.2; 435/290.3; 210/163

(58) Field of Classification Search .... 435/290.1–290.4; 210/163, 170.08; 4/520, 656; 47/1.4, 65.6; 52/302.3; 405/36; 71/9, 10, 12, 14
See application file for complete search history.

(56) References Cited

U.S. PATENT DOCUMENTS

| | | | |
|---|---|---|---|
| 4,400,195 A | 8/1983 | Rijkens | |
| 4,652,374 A | 3/1987 | Cohen | |
| 4,919,815 A | 4/1990 | Copa et al. | |
| 5,207,911 A | 5/1993 | Pellegrin et al. | |
| 5,269,634 A | 12/1993 | Chynoweth et al. | |
| 5,344,630 A | 9/1994 | Brendley, Jr. et al. | |
| 5,377,917 A | 1/1995 | Wiljan et al. | |
| 5,387,271 A | 2/1995 | Crawford et al. | |
| 5,389,258 A | 2/1995 | Smis et al. | |
| 5,403,798 A | 4/1995 | Brendley, Jr. et al. | |
| 5,407,817 A | 4/1995 | Lightsey et al. | |
| 5,431,819 A | 7/1995 | Hack et al. | |
| 5,492,624 A | 2/1996 | Rozich | |
| 5,500,123 A | 3/1996 | Srivastava | |
| 5,506,123 A | 4/1996 | Chieffalo et al. | |
| 5,529,692 A | 6/1996 | Kubler | |
| 5,571,703 A | 11/1996 | Chieffalo et al. | |

(Continued)

FOREIGN PATENT DOCUMENTS

CA    2061873 A1    5/1993

(Continued)

OTHER PUBLICATIONS

Blischke, J., Combining Anaerobic Digestion With Enclosed Tunnel Composting. BioCycle, 2004. 45(4): p. 49-68.

(Continued)

*Primary Examiner* — Michael Hobbs
(74) *Attorney, Agent, or Firm* — Choate Hall & Stewart LLP; William R. Haulbrook (57) ABSTRACT

This invention relates generally to systems and methods for digestion of solid waste that simplify solids handling. In certain embodiments, anaerobic methane extraction takes place for a period of time (e.g., from 1 to 4 weeks), after which an aerobic composting process begins in the same chamber. The organic waste remains in place and oxygen (e.g., in air) is forced into the chamber for an additional period of time (e.g., from 2 to 4 weeks). At the conclusion of the aerobic phase, the process yields a rough compost product that is stable and pathogen free. The rough compost can be further processed and blended to create high value engineered soils.

20 Claims, 5 Drawing Sheets

U.S. PATENT DOCUMENTS

| | | | |
|---|---|---|---|
| 5,601,720 | A | 2/1997 | Schmid |
| 5,630,942 | A | 5/1997 | Steiner |
| 5,670,047 | A | 9/1997 | Burke |
| 5,672,506 | A * | 9/1997 | Aoyagi et al. ............. 435/289.1 |
| 5,679,568 | A | 10/1997 | Imamura et al. |
| 5,746,919 | A | 5/1998 | Dague et al. |
| 5,773,283 | A | 6/1998 | Pierce |
| 5,773,526 | A | 6/1998 | Van Dijk et al. |
| 5,798,043 | A | 8/1998 | Khudenko |
| 5,866,754 | A | 2/1999 | De Blangy et al. |
| 5,885,460 | A | 3/1999 | Dague et al. |
| 5,919,696 | A | 7/1999 | Ikeda et al. |
| 5,928,859 | A | 7/1999 | Nicklin et al. |
| 5,958,756 | A * | 9/1999 | Reynell ........................ 435/262 |
| 5,962,305 | A | 10/1999 | Mihara et al. |
| 5,975,439 | A | 11/1999 | Chieffalo et al. |
| 6,004,772 | A | 12/1999 | Imamura et al. |
| 6,017,475 | A | 1/2000 | Cantrell |
| 6,017,746 | A | 1/2000 | Imamura et al. |
| 6,077,548 | A | 6/2000 | Lasseur et al. |
| 6,084,150 | A | 7/2000 | Crawford et al. |
| 6,110,727 | A | 8/2000 | Widmer et al. |
| 6,168,642 | B1 | 1/2001 | Valkanas et al. |
| 6,171,499 | B1 | 1/2001 | Bouchalat |
| 6,171,844 | B1 | 1/2001 | Numata et al. |
| 6,194,197 | B1 | 2/2001 | Hyman et al. |
| 6,197,081 | B1 | 3/2001 | Schmidt |
| 6,255,529 | B1 | 7/2001 | Nagase et al. |
| 6,267,309 | B1 | 7/2001 | Chieffalo et al. |
| 6,284,522 | B1 | 9/2001 | Wackett et al. |
| 6,342,378 | B1 | 1/2002 | Zhang et al. |
| 6,391,202 | B1 | 5/2002 | Knobloch et al. |
| 6,420,594 | B1 | 7/2002 | Farone et al. |
| 6,472,198 | B1 | 10/2002 | Semprini et al. |
| 6,521,444 | B1 | 2/2003 | Numata et al. |
| 6,551,510 | B1 | 4/2003 | Bakke et al. |
| 6,551,815 | B1 | 4/2003 | Nuttall et al. |
| 6,592,751 | B2 | 7/2003 | Haridas |
| 6,596,050 | B1 * | 7/2003 | Rihtamo et al. ..................... 71/9 |
| 6,630,517 | B2 | 10/2003 | Nishida et al. |
| 6,639,098 | B2 | 10/2003 | Farone et al. |
| 6,660,516 | B1 | 12/2003 | Imamura et al. |
| 6,660,518 | B1 | 12/2003 | Maekawa |
| 6,663,777 | B2 | 12/2003 | Schimel |
| 6,692,642 | B2 | 2/2004 | Josse et al. |
| 6,699,708 | B1 * | 3/2004 | Muller et al. ................. 435/262 |
| 6,719,902 | B1 | 4/2004 | Alvarez et al. |
| 6,737,263 | B2 | 5/2004 | Dragotta et al. |
| 6,783,679 | B1 | 8/2004 | Rozich |
| 6,824,686 | B2 | 11/2004 | Smis et al. |
| 6,878,212 | B1 | 4/2005 | Pinatti et al. |
| 6,896,804 | B2 | 5/2005 | Haerther et al. |
| 6,905,600 | B2 | 6/2005 | Lee, Jr. |
| 6,921,485 | B2 | 7/2005 | Kilian et al. |
| 6,939,444 | B2 | 9/2005 | Carlson, Jr. et al. |
| 6,991,931 | B2 | 1/2006 | Dragotta et al. |
| 6,995,007 | B2 | 2/2006 | Gunner et al. |
| 7,015,028 | B2 | 3/2006 | Choate et al. |
| 7,153,428 | B2 | 12/2006 | Chynoweth et al. |
| 7,160,456 | B2 | 1/2007 | Jarventie |
| 7,179,379 | B2 | 2/2007 | Appel et al. |
| 7,214,509 | B2 | 5/2007 | Schnoor et al. |
| 7,226,539 | B2 | 6/2007 | Dong et al. |
| 7,238,242 | B2 | 7/2007 | Pinatti et al. |
| 7,301,060 | B2 | 11/2007 | Appel et al. |
| 7,316,921 | B2 | 1/2008 | Choate et al. |
| 7,351,860 | B2 | 4/2008 | Adami et al. |
| 7,364,387 | B2 | 4/2008 | Kanitz et al. |
| 7,384,555 | B1 | 6/2008 | Yasui et al. |
| 7,442,348 | B2 | 10/2008 | Carlson, Jr. et al. |
| 7,476,296 | B2 | 1/2009 | Appel et al. |
| 7,485,230 | B2 | 2/2009 | Magner et al. |
| 7,560,266 | B2 | 7/2009 | Bramucci et al. |
| 7,582,467 | B2 | 9/2009 | Jarventie |
| 7,642,079 | B2 | 1/2010 | Cayouette et al. |
| 7,682,815 | B2 | 3/2010 | Guiot et al. |
| 7,692,050 | B2 | 4/2010 | Adams et al. |
| 7,781,191 | B2 | 8/2010 | Dunson, Jr. et al. |
| 7,833,414 | B2 | 11/2010 | Magner et al. |
| 7,854,840 | B2 | 12/2010 | Busch et al. |
| 2002/0039778 | A1 | 4/2002 | Wackett et al. |
| 2002/0061584 | A1 | 5/2002 | Farone et al. |
| 2002/0192132 | A1 | 12/2002 | Carlson et al. |
| 2003/0012710 | A1 | 1/2003 | Nishida et al. |
| 2003/0057152 | A1 | 3/2003 | Haridas |
| 2003/0121851 | A1 | 7/2003 | Lee |
| 2003/0152554 | A1 | 8/2003 | Gunner et al. |
| 2003/0173291 | A1 | 9/2003 | Schimel |
| 2003/0201224 | A1 | 10/2003 | Gannon et al. |
| 2003/0209489 | A1 | 11/2003 | Haerther et al. |
| 2003/0211594 | A1 | 11/2003 | Rosebrook |
| 2003/0213745 | A1 | 11/2003 | Haerther et al. |
| 2004/0043005 | A1 | 3/2004 | Gunner et al. |
| 2004/0152151 | A1 | 8/2004 | Dragotta et al. |
| 2004/0164020 | A1 | 8/2004 | De Baere et al. |
| 2004/0172878 | A1 | 9/2004 | Krylowicz et al. |
| 2004/0175819 | A1 | 9/2004 | Kanitz et al. |
| 2004/0182779 | A1 | 9/2004 | Kilian et al. |
| 2004/0188340 | A1 | 9/2004 | Appel et al. |
| 2004/0191755 | A1 | 9/2004 | Kemper et al. |
| 2004/0192980 | A1 | 9/2004 | Appel et al. |
| 2004/0192981 | A1 | 9/2004 | Appel et al. |
| 2004/0219650 | A1 | 11/2004 | Choate et al. |
| 2004/0237859 | A1 | 12/2004 | Hartmann |
| 2004/0262220 | A1 | 12/2004 | Binnig et al. |
| 2005/0011829 | A1 | 1/2005 | Dong et al. |
| 2005/0054030 | A1 | 3/2005 | Schnoor et al. |
| 2005/0113611 | A1 | 5/2005 | Adams et al. |
| 2005/0130290 | A1 | 6/2005 | Choate et al. |
| 2005/0155928 | A1 | 7/2005 | Jarventie |
| 2005/0161038 | A1 | 7/2005 | Pinatti et al. |
| 2005/0201831 | A1 | 9/2005 | Lee et al. |
| 2005/0238554 | A1 | 10/2005 | Carlson et al. |
| 2005/0245765 | A1 | 11/2005 | Adami et al. |
| 2005/0274668 | A1 | 12/2005 | Lee |
| 2006/0004237 | A1 | 1/2006 | Appel et al. |
| 2006/0060524 | A1 | 3/2006 | Chynoweth et al. |
| 2006/0096163 | A1 | 5/2006 | Dickinson et al. |
| 2006/0175252 | A1 | 8/2006 | Upendrakumar et al. |
| 2006/0177930 | A1 | 8/2006 | Bramucci et al. |
| 2006/0178387 | A1 | 8/2006 | Fujimoto-Ouchi et al. |
| 2006/0259995 | A1 | 11/2006 | Cayouette et al. |
| 2007/0029252 | A1 | 2/2007 | Dunson et al. |
| 2007/0031918 | A1 | 2/2007 | Dunson et al. |
| 2007/0031919 | A1 | 2/2007 | Dunson et al. |
| 2007/0031953 | A1 | 2/2007 | Dunson et al. |
| 2007/0037259 | A1 | 2/2007 | Hennessey et al. |
| 2007/0122874 | A1 | 5/2007 | Suthanthararajan et al. |
| 2007/0160524 | A1 | 7/2007 | Yoshida |
| 2007/0199613 | A1 | 8/2007 | Bouldin et al. |
| 2007/0218540 | A1 | 9/2007 | Guiot et al. |
| 2008/0011034 | A1 | 1/2008 | Hochrein et al. |
| 2008/0032382 | A1 | 2/2008 | Schnoor et al. |
| 2008/0038318 | A1 | 2/2008 | Tuomasjukka et al. |
| 2008/0138885 | A1 | 6/2008 | De Baere et al. |
| 2008/0193588 | A1 | 8/2008 | Yamamoto |
| 2008/0193989 | A1 | 8/2008 | Verser et al. |
| 2008/0199943 | A1 | 8/2008 | Widmer et al. |
| 2008/0201805 | A1 | 8/2008 | Krogh et al. |
| 2008/0206541 | A1 | 8/2008 | Medoff |
| 2008/0223793 | A1 | 9/2008 | Lee |
| 2008/0257108 | A1 | 10/2008 | Leberfinger et al. |
| 2008/0263956 | A1 | 10/2008 | Kuebler et al. |
| 2008/0314824 | A1 | 12/2008 | Busch et al. |
| 2009/0004714 | A1 | 1/2009 | Norholm et al. |
| 2009/0032458 | A1 | 2/2009 | Jensen et al. |
| 2009/0050134 | A1 | 2/2009 | Friend et al. |
| 2009/0053770 | A1 | 2/2009 | Hennessey et al. |
| 2009/0053800 | A1 | 2/2009 | Friend et al. |
| 2009/0111164 | A1 | 4/2009 | Schall et al. |
| 2009/0126274 | A1 | 5/2009 | Vogel et al. |
| 2009/0130733 | A1 | 5/2009 | Schmidt |
| 2009/0137015 | A1 | 5/2009 | Skudder |
| 2009/0148578 | A1 | 6/2009 | Kondoh et al. |
| 2009/0162923 | A1 | 6/2009 | Young et al. |
| 2009/0178671 | A1 | 7/2009 | Ahring et al. |
| 2009/0205173 | A1 | 8/2009 | Flaccomio Nardi Dei |

| | | | |
|---|---|---|---|
| 2009/0209025 A1 | 8/2009 | Goschl et al. | |
| 2009/0241623 A1 | 10/2009 | Matano et al. | |
| 2009/0250401 A1 | 10/2009 | Kotelko et al. | |
| 2009/0263876 A1 | 10/2009 | Atsumi et al. | |
| 2009/0283397 A1 | 11/2009 | Kato et al. | |
| 2009/0294355 A1 | 12/2009 | Menke et al. | |
| 2009/0305390 A1 | 12/2009 | Cacho et al. | |
| 2010/0028485 A1 | 2/2010 | Tuohy et al. | |
| 2010/0032369 A1 | 2/2010 | Bertolotto et al. | |
| 2010/0032370 A1 | 2/2010 | Allen et al. | |
| 2010/0069691 A1 | 3/2010 | Morschbacker | |
| 2010/0089822 A1 | 4/2010 | Terry | |
| 2010/0112242 A1 | 5/2010 | Medoff | |
| 2010/0162619 A1 | 7/2010 | Peus | |
| 2010/0178677 A1 | 7/2010 | Dunson, Jr. et al. | |

FOREIGN PATENT DOCUMENTS

| | | | |
|---|---|---|---|
| CA | 2587895 A1 | 5/2006 | |
| CA | 2592059 A1 | 1/2008 | |
| CH | 657604 A5 | 9/1986 | |
| CN | 1115209 A | 1/1996 | |
| CN | 1264969 A | 8/2000 | |
| CN | 1431159 A | 7/2003 | |
| CN | 1482105 A | 3/2004 | |
| CN | 2714565 Y | 8/2005 | |
| CN | 1772403 A | 5/2006 | |
| CN | 1903458 A | 1/2007 | |
| CN | 101015832 A | 8/2007 | |
| CN | 101058097 A | 10/2007 | |
| CN | 201003055 Y | 1/2008 | |
| CN | 101585043 A | 11/2009 | |
| CN | 101585044 A | 11/2009 | |
| CN | 101612630 A | 12/2009 | |
| DE | 19518234 A1 | 3/1996 | |
| DE | 102004053615 B3 | 5/2006 | |
| DE | 102005012936 A1 | 10/2006 | |
| DE | 102006005223 A1 | 8/2007 | |
| DE | 112006001877 A5 | 4/2008 | |
| EP | 0382340 A1 | 1/1990 | |
| EP | 0474895 A1 | 3/1992 | |
| EP | 0499302 A1 | 8/1992 | |
| EP | 0672457 A2 | 9/1995 | |
| EP | 0678085 A1 | 10/1995 | |
| EP | 0730027 A2 | 9/1996 | |
| EP | 0730031 A2 | 9/1996 | |
| EP | 0784039 A1 | 7/1997 | |
| EP | 0934998 A2 | 8/1999 | |
| EP | 1273362 A1 | 1/2003 | |
| EP | 1281753 A2 | 2/2003 | |
| EP | 1428868 A1 | 6/2004 | |
| EP | 1553058 A1 | 7/2005 | |
| EP | 1681274 A2 | 7/2006 | |
| EP | 2039775 A2 | 3/2009 | |
| ES | 2209613 A1 | 6/2004 | |
| GB | 2459881 A | 11/2009 | |
| JP | 10108670 A | 4/1998 | |
| WO | WO-9411278 A1 | 5/1994 | |
| WO | WO-9419119 A1 | 9/1994 | |
| WO | WO-9423857 A1 | 10/1994 | |
| WO | WO-9503259 A1 | 2/1995 | |
| WO | WO-9517517 A1 | 6/1995 | |
| WO | WO-9611891 A1 | 4/1996 | |
| WO | WO-9615081 A1 | 5/1996 | |
| WO | WO-9634841 A1 | 11/1996 | |
| WO | WO-9732829 A1 | 9/1997 | |
| WO | WO-9734851 A1 | 9/1997 | |
| WO | WO-9743432 A1 | 11/1997 | |
| WO | WO-9947473 A1 | 9/1999 | |
| WO | WO-0039255 A1 | 7/2000 | |
| WO | WO-0100341 A1 | 1/2001 | |
| WO | WO-0136340 A1 | 5/2001 | |
| WO | WO-0156715 A1 | 8/2001 | |
| WO | WO-0156938 A1 | 8/2001 | |
| WO | WO-0231104 A2 | 4/2002 | |
| WO | WO-0231175 A1 | 4/2002 | |
| WO | WO-02051561 A2 | 7/2002 | |
| WO | WO-03035560 A1 | 5/2003 | |
| WO | WO-03059825 A1 | 7/2003 | |
| WO | WO-03082747 A1 | 10/2003 | |
| WO | WO-2004020382 A1 | 3/2004 | |
| WO | WO-2004076082 A1 | 9/2004 | |
| WO | WO-2006039354 A2 | 4/2006 | |
| WO | WO-2006039355 A2 | 4/2006 | |
| WO | WO-2006102543 A2 | 9/2006 | |
| WO | WO-2007012328 A1 | 2/2007 | |
| WO | WO-2007047063 A2 | 4/2007 | |
| WO | WO-2007093398 A2 | 8/2007 | |
| WO | WO-2007139264 A1 | 12/2007 | |
| WO | WO-2007146922 A2 | 12/2007 | |
| WO | WO-2008025098 A1 | 3/2008 | |
| WO | WO-2008081407 A2 | 7/2008 | |
| WO | WO-2008081408 A2 | 7/2008 | |
| WO | WO-2008081409 A2 | 7/2008 | |
| WO | WO-2008081410 A2 | 7/2008 | |
| WO | WO-2009012772 A2 | 1/2009 | |
| WO | WO-2009044076 A2 | 4/2009 | |
| WO | WO-2009063103 A1 | 5/2009 | |
| WO | WO-2009072887 A1 | 6/2009 | |
| WO | WO-2009103866 A2 | 8/2009 | |
| WO | WO-2009108069 A1 | 9/2009 | |
| WO | WO-2009108761 A1 | 9/2009 | |
| WO | WO-2009135967 A1 | 11/2009 | |
| WO | WO-2009150455 A2 | 12/2009 | |
| WO | WO-2010019935 A2 | 2/2010 | |
| WO | WO-2010056940 A2 | 5/2010 | |
| WO | WO-2010082741 A2 | 7/2010 | |

OTHER PUBLICATIONS

La Brooy et al., "The UR-3R Facility: A Fully Integrated Approach to Municipal Solid Waste Management," Proceedings for ORBIT 2003, pp. 47-56.

Cecchi, F.; Traverso, P. G.; Mata-Alvarez, J.; Clancy, J.; Zaror, C., Biomass, State of the Art of R&D in the Anaerobic Digestion Process of Municipal Solid Waste in Europe, 1988, 16, 257-284.

Chan et al., "Effects of leachate recirculation on biogas production from landfill co-disposal of municipal solid waste, sewage sludge and marine sediment," Environmental Pollution 118 (2002) 393-399.

Gallert et al., Bio- and Pyrotechnology of Solid Waste Treatment, *Biotechnology Second, Completely Revised Edition, 2000.*

Legros, A.; Dujardin, E.; Collard, F.; Naveau, H.; Nyns, E. J.; Sironval, C.,Energy from biomass: 3rd E.C. Conference "An Integrated System: Mass Algae Culture in Polluted Luke-Warm Water for Production of Methane, High-Value Products and Animal Feed," (International conference on biomass, Venice, 1985).

Mata-Alvarez, J. (1999), Biomethanization of Organic Fraction of Municipal Solid Wastes, London, 336-367 (Accessed: May 30, 2010).

Nichols, C.E., Overview of anaerobic digestion technologies in Europe. BioCycle, 2004. 45(1): p. 47-53.

Schalk, Combined Mechanical and Biological Treatment of Municip Solid Waste, *Biotechnology Second, Completely Revised Edition*, 2000.

Vandevivere, De Baere, Verstraete, Types of anaerobic digesters for solid wastes, 2002.

Viéitez and Ghosh, "Biogasification of solid wastes by two-phase anaerobic fermentation," Biomass and Bioenergy 16 (1999) 299-309.

Rapport et al., "Current Anaerobic Digestion Technologies Used for Treatment of Municipal Organic Solid Waste," California Intergrated Waste Management Board, Mar. 2008, 90 pages.

Biswas, R., Uellendahl, H., and Ahring, B.K. (2010). Increasing the biogas yield of manure by wet explosion of the digested fiber fraction—lab-scale optimization and large-scale implementation. Proceedings 12th World Congress on Anaerobic Digestion, Oct. 31-Nov. 4, 2010, Guadalajara, Mexico.

Hartmann, H., and Ahring, B.K. (2006). Strategies for the anaerobic digestion of the organic fraction of municipal solid waste. Water Science and Technology 53 (8), 7-22.

Sørensen, A.H., Winther-Nielsen, M., and Ahring, B.K. (1991) Kinetics of lactate, acetate and propionate in unadapted and lactate-adapted thermophilic, anaerobic sewage sludge—the influence of sludge adaptation for start-up of thermophilic UASB reactors. Applied Microbiology and Biotechnology 34 (6), 823-827.

\* cited by examiner

SYSTEMS AND METHODS FOR DIGESTION OF SOLID WASTE

RELATED APPLICATION

This application claims priority to and the benefit of U.S. provisional patent application Ser. No. 61/505,696, filed Jul. 8, 2011, the disclosure of which is incorporated herein by reference in its entirety.

FIELD OF THE INVENTION

This invention relates generally to the digestion of solid waste. More particularly, in certain embodiments, the invention relates to apparatus and methods for decomposing organic matter into biogas and compost.

BACKGROUND OF THE INVENTION

The degradation of organic matter is a process that occurs aerobically and/or anaerobically in nature by the complex interaction of a multitude of microorganisms. Controlled more or less industrialized methods have been known for a long time and referred to as composting for aerobic processes and fermentation, bio-methanisation, or simply anaerobic digestion (AD), for the anaerobic processes. AD processes may be divided into two principle steps: hydrolysis and methanogenesis.

The two processes of composting and AD have been developing independently over the last many years. Composting as a way to produce compost for fertilization and soil improvement has been thoroughly described many places. Likewise, one-stage, two-stage, or multi-stage AD methods have been developed on the basis of the most varied developments. In addition to wet AD developed from liquid-manure and waste-water treatment, dry AD is also practiced.

The principle of the two-step, two-stage AD was described for the first time by Ghosh in 1978. In this process, wastes are percolated in an anaerobic reactor. The percolation water is subsequently fermented to biogas in a methane reactor. The method was further developed and patented by Rijkens and Hofank (U.S. Pat. No. 4,400,195) in the 1980s for organic wastes. The method was converted twice to practice, to the ANM method in Ganderkesee and to the Prethane-Rudad method in Breda. Tests were conducted by Wellinger and Suter in the 1980s with solid manure, and by Widmer with market and meatpacking wastes. In the latter case, the percolator was also driven in an aerobic environment.

The newest plants, which have been developed according to this method (for residual wastes) are the ISKA® percolation method in Sansenheck, and the BIOPERCOLAT® method (DE 198 46336 A1). Here, the waste is hydrolyzed in a percolator after a mechanical pretreatment (for example, sieving, metal separation). The percolator is therefore equipped with a stirring mechanism, so that the wastes are continually transported through the reactor. After a residence time of 2 to 3 days, the percolate is discharged free of water and ready for further treatment or depositing in a layer. The percolation water is fermented anaerobically to biogas in a methane reactor after separation of sand and fibers. The water that is cleaned in this way is directly used as percolation water or is used after another cleaning (e.g., for removing nitrogen).

Large amounts of organic solid wastes are produced in many towns and cities all over the world, and treatment methods are often limited by solids handling requirements for adequate sterilization of these large amounts of heavy, solid waste. Accordingly, there is a need for improved systems and methods for digestion and composting of solid wastes with limited solids handling requirements.

SUMMARY OF THE INVENTION

A system is presented for solid waste treatment that does not require moving the solid fraction of the waste between different stages of the process. Only initial loading of the waste and final unloading of the solids after sanitization is needed.

In one embodiment, organic waste is loaded into a chamber that resembles a garage. After filling, the door is closed and anaerobic conditions are created. Anaerobic methane extraction takes place for a period of time (e.g., from 1 to 4 weeks), after which an aerobic composting process begins in the same chamber. The organic waste remains in place and oxygen (e.g., in air) is forced into the chamber for an additional period of time (e.g., from 2 to 4 weeks). At the conclusion of the aerobic composting phase, the process yields a rough compost product that is stable and pathogen free. The rough compost can be further processed and blended to create high value engineered soils. There is no requirement to handle raw, post-methane extraction digestate prior to composting. The biogas produced has a high methane content, e.g., about 70% or more, compared to about 55-60% using other processes. The biogas also has lower concentrations of VOC's, siloxane, and other contaminants.

The system employs dry anaerobic digestion in which bacterial hydrolysis—that is, the leaching out of fatty acids from the organic solid waste—is physically separated from methane generation. A series of hydrolysis and methane generation (gasification) stages are conducted for a period of time (e.g., from 1 to 4 weeks) under anaerobic conditions with the solid waste in a waste processing tank operating at ambient (e.g., atmospheric) pressure. Percolate liquid is recirculated through a grating at or near the base of the waste processing tank during the hydrolysis stage. The percolate is pumped into a biogas reactor tank in which methane and/or other biogases are produced, then filtered, degassed percolate is pumped back to the waste processing tank. After hydrolysis and gasification is completed, the waste processing tank becomes a composter, such that air flows through the solid waste, through the grating at the base, then passes through a biofilter before being released into the atmosphere. After composting, the solid waste is sufficiently sanitary for removal and may be safely disposed or used as a byproduct.

During all three stages—hydrolysis, gasification, and composting—the waste processing tank remains closed. No solid waste is moved, and only fluids and air circulates between the process module and the gas reactor in a closed system. The system design insures that the processes of hydrolysis, percolation, methane generation, and composting are separate and occur rapidly and efficiently. There is no need for inoculation using earlier processed material to start fresh batches, thereby insuring full traceability of the waste. The process is self-sustaining and there is no need for heating to start the process, allowing for a high energy efficiency. A wide variety of organic waste types may be processed, for example, municipal waste; industrial, commercial, and institutional waste; garden waste; and sewage sludge.

Thus, in one aspect, the invention relates to a system for decomposition of organic matter into biogas and compost, the system including: a waste processing tank into which solid organic waste is loaded and in which hydrolysis and composting takes place at separate times, with composting of the solid organic waste taking place during a separate stage after hydrolysis is completed, wherein the waste processing tank comprises a drain at or near its base, the drain allowing flow of percolation liquid out of the waste processing tank during the hydrolysis stage, the drain also serving as a vent through which air flows into and/or out of the solid organic waste in the waste processing tank during the composting stage; a spraying system configured to spray percolate liquid onto the solid organic waste in the waste processing tank during the hydrolysis stage, wherein the percolate liquid comprises fatty acids leached from the solid organic waste and wherein the percolate liquid is recycled from the base of the waste processing tank during the hydrolysis stage; and a biogas reactor tank into which the percolate liquid from the waste processing tank is pumped for generation of biogas under anaerobic conditions during a gasification stage. In certain embodiments, the waste processing tank is configured to operate at ambient pressure during the hydrolysis stage, the composting stage, or both. In preferred embodiments, the waste processing tank is configured to operate under anaerobic conditions during the hydrolysis stage.

In certain embodiments, the system further includes a biofilter through which air from the waste processing tank passes prior to discharge to the atmosphere during the composting stage. In certain embodiments, the system further includes a filter configured to separate solids from the percolate liquid.

In certain embodiments, the system includes at least two waste processing tanks connected in parallel. In certain embodiments, the waste processing tank includes an acid-resistant lining or coating. The biogas reactor tank is preferably gas-tight. The system may also include a heater for heating the percolate liquid either in the biogas reactor tank or outside the biogas reactor tank (for later introduction back into the tank after heating). In certain embodiments, the biogas reactor tank includes a sump to separate sediment and/or particles from the percolate liquid.

In preferred embodiments, the system further includes a liquid process tank into which percolate liquid from either the biogas reactor tank, the waste processing tank, or both flows prior to being pumped to the spraying system for spraying onto the solid organic waste in the waste processing tank during the hydrolysis stage. In certain embodiments, there is one liquid process tank for every waste processing tank. In certain embodiments, there is at least five waste processing tanks (e.g., each with their own associated liquid process tank), for every biogas reactor tank (there may be one or more biogas reactor tanks in the system). In certain embodiments, percolate liquid from both the biogas reactor and the waste processing tank flows into the liquid process tank prior to being pumped to the spraying system for spraying onto the solid organic waste in the waste processing tank during the hydrolysis stage. The system may further include a filter tank configured to separate solids from the percolate liquid before the percolate liquid enters the liquid process tank.

Elements of other aspects of the invention can be applied to this aspect of the invention as well.

In another aspect, the invention relates to a method for decomposition of organic matter into biogas and compost, the method including the steps of: (a) loading solid organic waste into a waste processing tank; (b) during one or more series of hydrolysis and gasification stages: (i) spraying percolation liquid over the solid organic waste in the waste processing tank during a first (and/or subsequent) hydrolysis stage in which bacterial hydrolysis takes place; (ii) optionally recirculating the percolation liquid after it passes through the solid organic waste in the waste processing tank during the first (and/or subsequent) hydrolysis stage; (iii) pumping percolation liquid into a biogas reactor tank for generation of biogas during a first (and/or subsequent) gasification stage; (iv) pumping percolate liquid out of the biogas reactor tank following the first (and/or subsequent) gasification stage, for spraying over the solid organic waste in the waste processing tank during a second and/or subsequent hydrolysis stage; and (c) following all hydrolysis and gasification stages, ventilating the waste processing tank for composting of the solid organic waste under aerobic conditions.

In certain embodiments, the series of hydrolysis and gasification stages is carried out for a period of from 1 to 4 weeks (e.g., for about 21 days) before the composting stage begins. In certain embodiments, methanogenesis takes place in the biogas reactor tank during the gasification stage. In preferred embodiments, the hydrolysis and gasification stages take place under anaerobic conditions. In certain embodiments the one or more hydrolysis stages (and/or the gasification stage(s)) take place under atmospheric pressure. Hydrolysis generally takes place at the same time as gasification, but the processes occur in different tanks.

In certain embodiments, the percolation liquid is passed through a filter tank configured to separate solids from the percolate liquid, then the filtered liquid is transported into a liquid process tank where it mixes with liquid from the biogas reactor tank before being recirculated via spraying over the solid organic waste in the waste processing tank. In certain embodiments, the percolation liquid enters a process tank where it mixes with liquid from the biogas reactor tank before being recirculated via spraying over the solid organic waste in the waste processing tank.

In certain embodiments, the method comprises flooding the waste processing tank with percolation liquid at least once during the hydrolysis stage.

In certain embodiments, the temperature of the organic solid waste in the waste processing tank reaches at least 60° C. during at least part of the composting stage. In preferred embodiments, the method further includes the step of passing air through a biofilter after it has passed through the solid organic waste in the waste processing tank during the composting stage. In certain embodiments, the solid organic waste in the waste processing tank has been sanitized by the end of the composting stage.

The description of elements of the embodiments above can be applied to this aspect of the invention as well.

In another aspect, the invention relates to a dual-purpose drain assembly for transport of percolate from a process module during a digestion stage and for ventilation of the process module during a composting stage of a waste processing system, the drain assembly including one or more rails through which a plurality of conduits are drilled, wherein each of the conduits has (i) a first end facing the process module containing solid waste being processed and (ii) a second end facing a pipe through which liquid percolate flows out of the process module during hydrolysis and through which air flows into the process module during composting, wherein the first end has a width or diameter smaller than the second end's. In certain embodiments, the first end has a diameter (or width) no greater than 90% of that of the second end. In certain embodiments, the ratio of the diameter of the first end to the diameter of the second end is about 0.75.

In certain embodiments, each of the rails has a notch, and two or more of such notched rails form a shelf for supporting a removable plate (e.g., stainless steel plate) that prevents the solid waste in the waste processing module from entering the pipe. In certain embodiments, the pipe is a conduit formed in a concrete base below the process module.

Elements of other aspects of the invention can be applied to this aspect of the invention as well.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

DETAILED DESCRIPTION

It is contemplated that apparatus, devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where apparatus, devices and systems are described as having, including, or comprising specific components, or where processes and methods are described as having, including, or comprising specific steps, it is contemplated that, additionally, there are apparatus, devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

It is contemplated that methods, systems, and processes of the claimed invention encompass scale-ups, variations, and adaptations developed using information from the embodiments described herein. The processes and methods described herein may be performed using reactor equipment that is known to those of ordinary skill in the art, including, without limitation, for example, batch reactors, plug-flow reactors, continuously-stirred tank reactors, packed-bed reactors, slurry reactors, fluidized bed reactors, and columns. The processes described herein may be conducted in batch, semi-continuous, and/or continuous operation, or adapted therefor. It is also contemplated that methods, systems, and processes of the claimed invention may include pumps, heat exchangers, and gas-, liquid-, and/or solid-phase material handling equipment known to those of ordinary skill in the art.

The mention herein of any publication, for example, in the Background section, is not an admission that the publication serves as prior art with respect to any of the claims presented herein. The Background section is presented for purposes of clarity and is not meant as a description of prior art with respect to any claim.

In certain embodiments, the invention relates to a method for converting organic matter into biogas and compost. The organic matter may be sorted and mixed with green structure, introduced in a process module, where percolate, recycled in a process tank, washes out nutrients (e.g., volatile fatty acids). Excess percolate may be pumped through a coarse filter to a reactor tank where the anaerobic digestion takes place. Biogas produced in the reactor tanks may be transported to utilization. Degassed percolate may then be returned to the process tank for washing out additional nutrients from the organic matter.

In another embodiment, after a period of time, and when the pH reaches a specified value, the percolation process is stopped, an air-intake is opened, and through the drain system, used for percolation, air is drawn through the organic matter to initiate the composting process. After composting, the process modules are emptied, and the material is left in open bays for after maturation, until it is sorted and the final soil improvement products ready for market.

In certain embodiments, the two-stages (AD and composting) are combined with a time-dependent and physical split of the AD process in hydrolysis and methanogenesis. For example, in a first process cycle, percolation of dry organic matter causes hydrolytes (such as volatile fatty acids, etc.) to be extracted, and the percolate (the wet fraction) is delivered to a biogas reactor tank for methanogenesis. In one embodiment, the hydrolysis takes place under anaerobic conditions. Hydrolysis may be accomplished in the solid phase, followed by methanogenesis in the wet phase, followed by methanogenesis in the solid phase, and finally composting of the dry phase.

In certain embodiments, AD and composting are achieved using specialized process modules (PM) and a methane reactor (MR). In one embodiment, a mixture of structure and organic matter is loaded into the PMs, and one or more gates to the PMs are closed. Run off (i.e., percolate) containing hydrolytes from the PM may be delivered to a process tank (PT) prior to transfer to the MR.

In certain embodiments, degassed liquid from the MR is returned to the PT, from which it may be sprayed onto the organic matter in the PM. The percolate from the PM may be fed back to the process tank, through a drain in the bottom of the PM. In one embodiment, the process module is operated under anaerobic conditions during percolation. Excess percolation liquid, now containing hydrolytes, may be fed through a coarse filter, and introduced into the MR, where the methanogenesis takes place. Separation of fresh and degassed percolate may take place using a principle of leveling in the reactor tank. Percolate may be continuously taken out of the MR and heated in a heat exchanger.

When the pH of percolate coming out of the process module has reached a defined level, and the solid fraction in the PM has been inoculated by methanogenic bacteria, the methanogenesis may start in the PM. After a period of time, the methane production or accumulation in the PM is stopped. In one embodiment, for example, an air intake is opened and a fan starts to draw air (including oxygen) through the organic matter still contained and enclosed in the process modules. During this portion of the process, when composting takes place, the process module is operated under aerobic conditions. In another embodiment, the air is introduced or extracted through the same drain as that the percolation fluid passes through during percolation.

The introduction of air may start a composting process of the organic matter in the process modules. In certain embodiments, this causes the temperature to increase, and a sanitization process will take place. Further, water may evaporate from the organic matter, thereby reducing the moisture content. After leaving the organic matter, the air may be fed through a biofilter and an optional scrubber for elimination of odors.

In certain embodiments, when the temperature of the organic matter in the process module has reached a defined level, or the composting process has taken place for a specific period of time, the fan is stopped. At this point, a door or gate the process module may be opened, and the degassed and composted organic matter may be taken out of the process module. The organic matter may then be left outside in open bays for after maturation, before final screening and mixing for compost or soil improvement products.

In certain embodiments, a decomposing method for organic matter is provided in which an amount of biogas is formed according to need. An anaerobically driven process module may be loaded with a mixture of structure and organic matter. In one embodiment, a percolation liquid is sprayed onto the organic matter, led through the bottom of the process module to a process tank, from where is again sprayed on the organic matter. In another embodiment, excess percolation liquid is passed through a coarse filter into a reactor tank, where it is fermented to biogas. The degassed percolate may be fed back to the process tank.

The decomposing methods described herein are advantageously based on a simple and robust process. In this way, control of the biogas formed according to need is made possible, and a biogas requirement, for example, for conversion to electrical energy or production of heat at peak times or times of low demand, can be controlled accordingly. While control of biogas production may not be provided or may be provided only in constricted periods for adapting to consumption in known plants, a rapid adaptation to the current requirement can be provided with the decomposing method, in accordance with an embodiment of the invention.

All substances originating from living organisms may be considered to be biogenic materials, including, in particular, the following: bio-wastes, lawn cuttings, curbside clippings, garden clippings, bio-solids, industrial waste, food waste, household waste, agricultural waste, kitchen waste, renewable resources, and similar materials.

Since, in certain embodiments, hydrolysis and methanogenesis are physically and time-wise separated, the biogas contains low concentration of sulphur, and silicas, thus cleaning of $H_2S$ and $SiO_x$ is not necessary when applying the biogas for heat and power production in an IC engine.

In one embodiment of the invention, the construction of the bottom of the process module, used for percolate discharge and air exhaust, is performed in a manner so blocking does not occur. In this way, the design may ensure that percolate and air always have free passage during operation.

As mentioned, in certain embodiments, the atmosphere is anaerobic during percolation and aerobic during composting. It is further possible to insulate or even heat the PMs. For example, the temperature in the process module may be approximately 38° C. under percolation and 70° C. during composting.

In certain embodiments, all of the liquid in the system is pumped through one circuit. The percolation liquid leaving the reactor tank, as degassed percolate, may be discharged discontinuously and replaced with fresh, hydrolyte rich liquid. In this way, a concentration of foreign matter in the circuit may be avoided. In another embodiment, substances that sink and/or float are separated in the reactor tank in a sump, equipped with a pump that is able to remove sludge.

In certain embodiments, methanogenesis of the percolate to biogas is conducted by means of bacteria. In this case, the methanogenesis may be conducted with the participation of a bacterial matrix of several bacterial strains. The methane reactor can be heated; for example, it can be heated by taking out a slipstream of liquid and heating the liquid in a heat-exchanger before it is introduced again into the reactor tank. In this way, a constant temperature can be maintained in the biogas reactor. The temperature within the biogas reactor may be, for example, between about 38° C. or 55° C.

In addition, in certain embodiments, the an apparatus is provided that includes at least one process module, a process tank, a filter tank, and a reactor tank. The process module may be equipped with at least one pump and one fan. The methane reactor tank can be, for example, CSTR, UASB, or another type for AD. Compared previous systems, because the process step of methanogenesis occurs in the MR, overfeeding is much less likely to occur and it is easier to control and/or measure.

Preferably, in one embodiment, the biogas plant includes at least five parallel-connected process modules. In this case, the percolation liquid may be sprayed continuously or discontinuously over the organic matter. Spraying may be performed by a separate pump for each process module through a specially designed spraying system, depending on the material used. For example, a separately operable liquid circuit may be formed for each process module. A connection between one or more individual percolators may be used to inoculate the organic matter with specific species of bacteria.

The use of at least two percolators, in some embodiments, has the advantage that a loading and unloading of solid materials is possible at any given time. In addition, the substrate specific residence time in each process module can be controlled individually.

Due to acids that may be formed during the decomposition process, the process modules are preferably acid-resistant. In certain embodiments, the percolation liquid dissolves the acids and/or other materials that form, and/or the percolation liquid is enriched with hydrolytes that can be easily transformed to methane.

In one embodiment, the process modules have a special designed bottom. During percolation, the bottom of the process modules is used to perform a solid-liquid separation, where the separated percolation liquid collects under the drain and is sprayed continuously or discontinuously in the circuit over the organic matter by means of pumps. Excess percolation liquid may be pumped into the buffer tank with appropriate filling level, and from there into the biogas process reactor. During composting, the bottom of the process tanks may be used for air discharge, after the air has passed through the organic matter. The temperature in the process modules may be approximately 38° C. The process modules may be insulated and/or heated.

In certain embodiments, the AD is provided by means of added and/or immobilized bacteria, which are continuously prevailing and produced in the methane reactor. The methane reactor tank may be essentially gas-tight and/or may function according to a reactor principle that is common to wastewater technology. For example, the reactor tank may be an Up-flow Anaerobic Sludge Bed (UASB-sludge bed), a solid bed reactor, and/or a Continuously Stirred Tank Reactor (CSTR). A solid bed biogas reactor tank can be, for example, operated as a plug flow reactor, so that both the residence time in the process module as well as the residence time in the biogas reactor tank can be defined and controlled.

In certain embodiments, the biogas includes methane ($CH_4$) [e.g., 50-85 vol. %], carbon dioxide ($CO_2$) [e.g., 15-50 vol. %], as well as oxygen, nitrogen, and trace gases (including hydrogen sulfide). A biogas with a high methane fraction of between about 65 and about 80 vol. %, or more, may be produced with the decomposing method according to the invention.

Among other things, the biogas can be used directly for heating purposes or, by means of a block-type thermal power system (IC engine, Fuel Cell, Turbine), for the coupled production of electricity and heat, or it can be upgraded for introduction in pipeline systems or used for vehicle fuel. In various embodiments, the gas is produced by anaerobic digestion of organic matter.

To increase the biogas yield, co-materials (for example, renewable resources or wastes from the food industry) can be used. The AD and composted organic matter can subsequently be evaluated as high-value fertilizer for agricultural use.

In certain embodiments, during the methanogenesis, a slip-stream of the percolate leaves the reactor tank, is heated in a heat exchanger or other heating device, before being reintroduced in the reactor tank. In this way, a constant temperature can be maintained in the biogas reactor tank. The temperature in the biogas reactor tank may be between about 38° C. and about 55° C. In certain embodiments, the temperature in the biogas reactor tank is about 38° C., or about 55° C.

An accumulation of the most varied substances in the percolate can be avoided, as a mechanism in the bottom of the reactor tank (e.g., a sump) allows particles to be continuously or frequently removed from the process.

Figure 1:
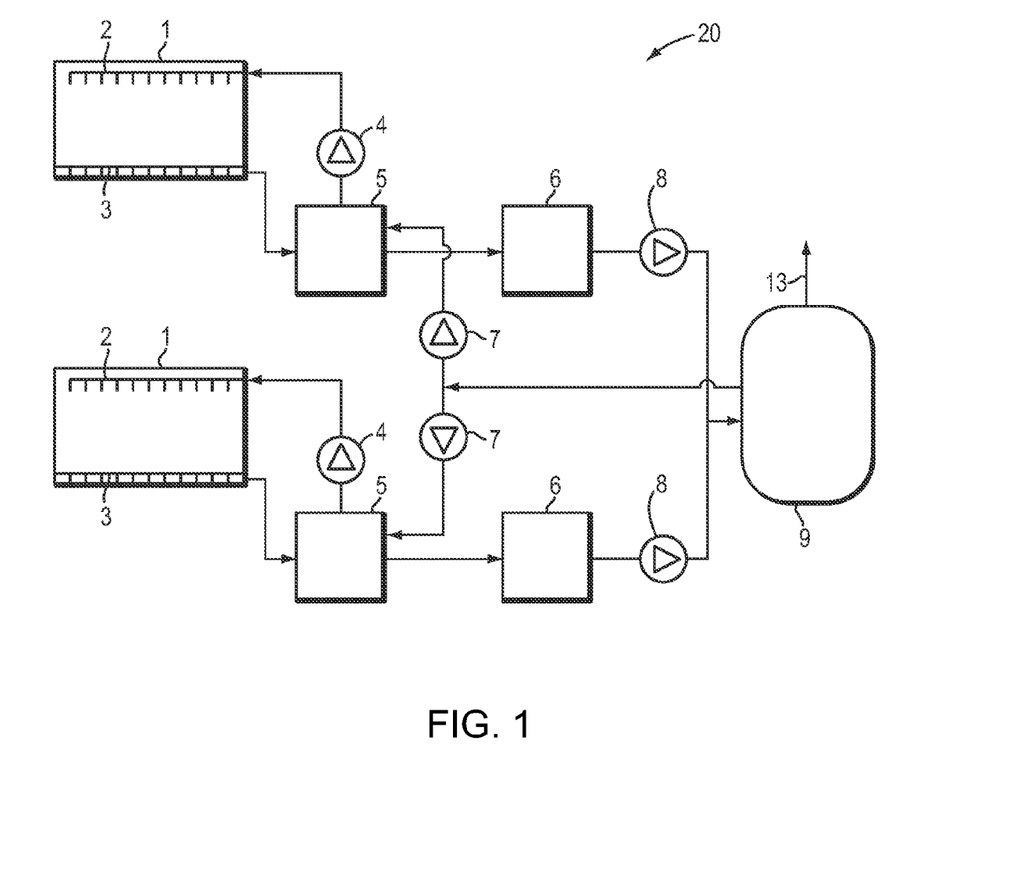
FIG. 1 is a schematic drawing of an apparatus for digestion and composting of solid waste, highlighting components involved in the hydrolysis and methanogenesis stages, in accordance with an embodiment of the invention.

FIG. 1 depicts an apparatus 20 for digestion of solid waste, in accordance with an embodiment of the invention. In one embodiment, the process tank 1 operates at ambient pressure. Liquid percolates through organic matter in the process tank 1 and exits through a draining system (a grating) 3 at the bottom. The percolate is collected in a process tank 5, then pumped to a spraying system 2 back into the process tank 1 with a pump 4. Excess percolation liquid is pumped into a filter tank 6 by another pump 8, where it is filtered, then is pumped into a biogas reactor tank 9. Degassed percolation liquid is discharged from the biogas reactor tank 9 and returned to the process tank 5.

Process modules 1 are constructed as a type of "garage" or container, with an acid-resistant lining. The process modules 1 are configured such that they are charged by the usual technological means (for example, with wheel loaders). A bottom of the process modules 1 includes a drain system 3 so that a solid-liquid separation can occur. The drain system 3 is designed and constructed to prevent blocking or clogging. The process modules 1 may operate at ambient pressure.

The percolation liquid is drained or percolated through organic matter and exits the process modules 1 through the draining system 3 at the bottom of the process modules 1. The percolate is collected in process tanks 5, from which it is pumped to a spraying system 2 in the process modules 1. The spraying system 2 continuously or discontinuously sprays the liquid over the organic matter in the process modules 1 by means of pumps 4.

During operation of the apparatus 20, the percolation liquid dissolves the acids, volatile fatty acids, and other substances from the solid organic waste bed. As a result, the percolation liquid is enriched with easily digestible substances.

From the process tanks 5, excess percolation liquid is pumped via pumps 8 into filter tanks 6 having an appropriate filling level. The filter tanks 6 are equipped with a coarse filter where bigger pieces (e.g., large solids) can be separated from the liquid stream.

From there, the percolation liquid is pumped in a gas-tight manner into a biogas reactor 9 by means of pumps 8. The biogas reactor 9 functions according to a reaction principle that is common for wastewater technology (e.g., UASB, CSTR, sludge bed, solid bed reactor). Inside the biogas reactor 9, the percolation liquid is digested rapidly into exiting biogas 13, containing mainly $CH_4$ and $CO_2$. The degassed percolation liquid is discharged from the biogas reactor 9 and returned to the process tanks 5 using pumps 7.

Figure 2:
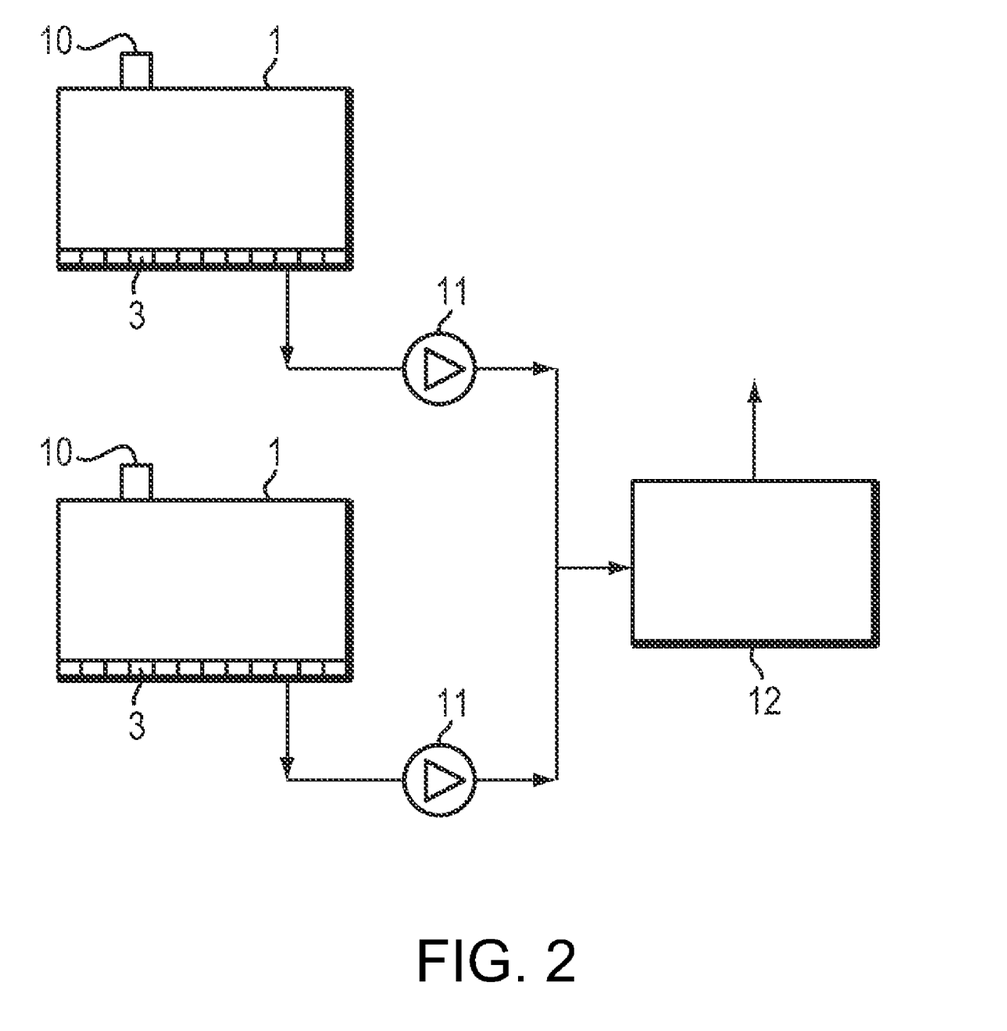
FIG. 2 is a schematic drawing of an apparatus for digestion and composting of solid waste, highlighting components involved in the composting stage, in accordance with an embodiment of the invention.

FIG. 2 depicts an apparatus for composting solid waste, in accordance with an embodiment of the invention. After the hydrolysis and methanogenesis stages depicted in FIG. 1, the conditions in the process modules 1 shifts from anaerobic (with percolation) to aerobic, as air is introduced. In the depicted embodiment, air intakes 10 mounted on top of the process modules 1 are opened and pumps 11 start to draw air continuously or discontinuously (e.g., intermittently) through the already percolated organic matter. After passing through the organic matter, the air is discharged through a biofilter 12, where odors are scrubbed (e.g., using microorganisms) from the air.

Figure 3:
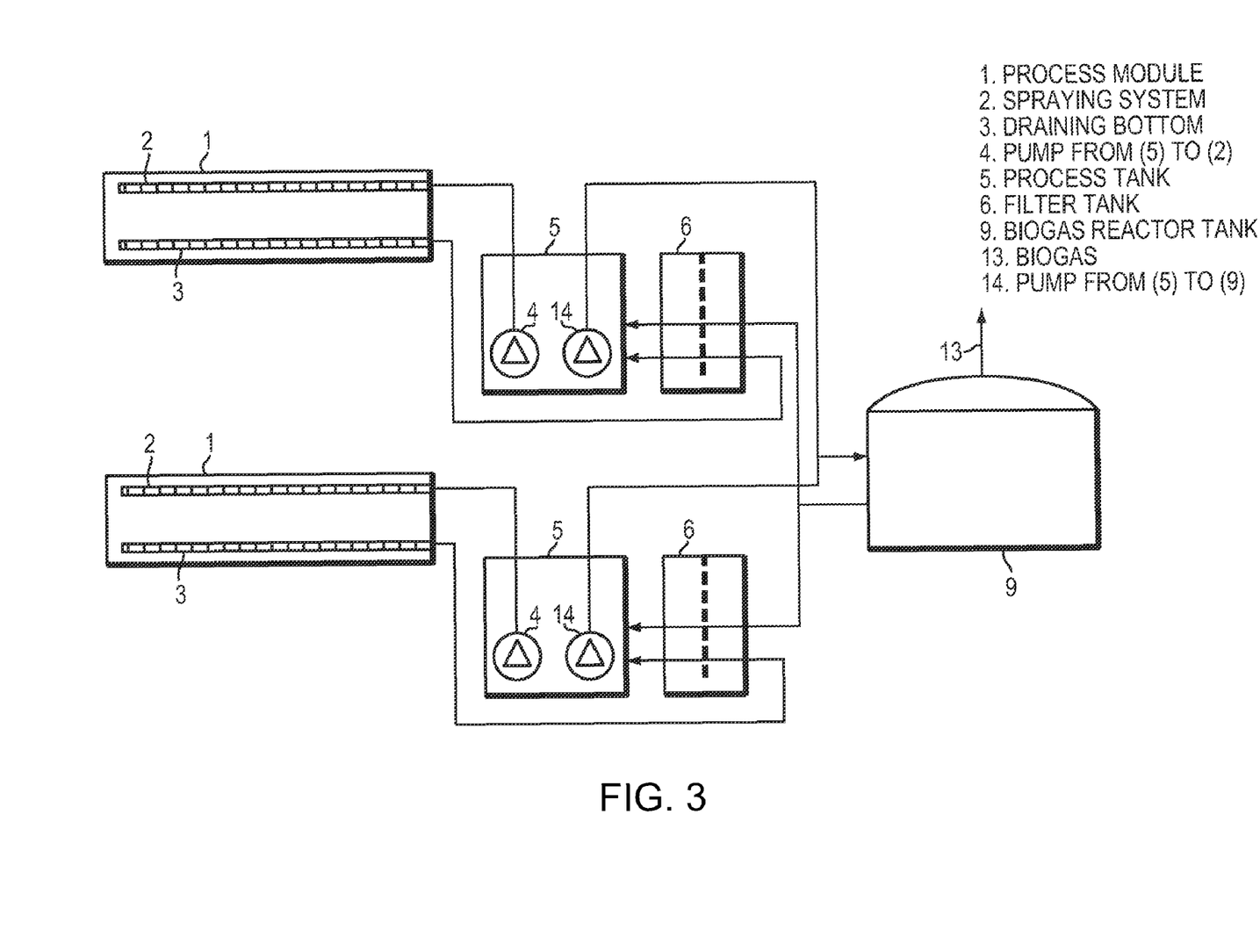
FIG. 3 is a schematic drawing of an apparatus for digestion and composting of solid waste, highlighting components involved in the hydrolysis and methanogenesis stages, in accordance with an embodiment of the invention.
Figure 4:
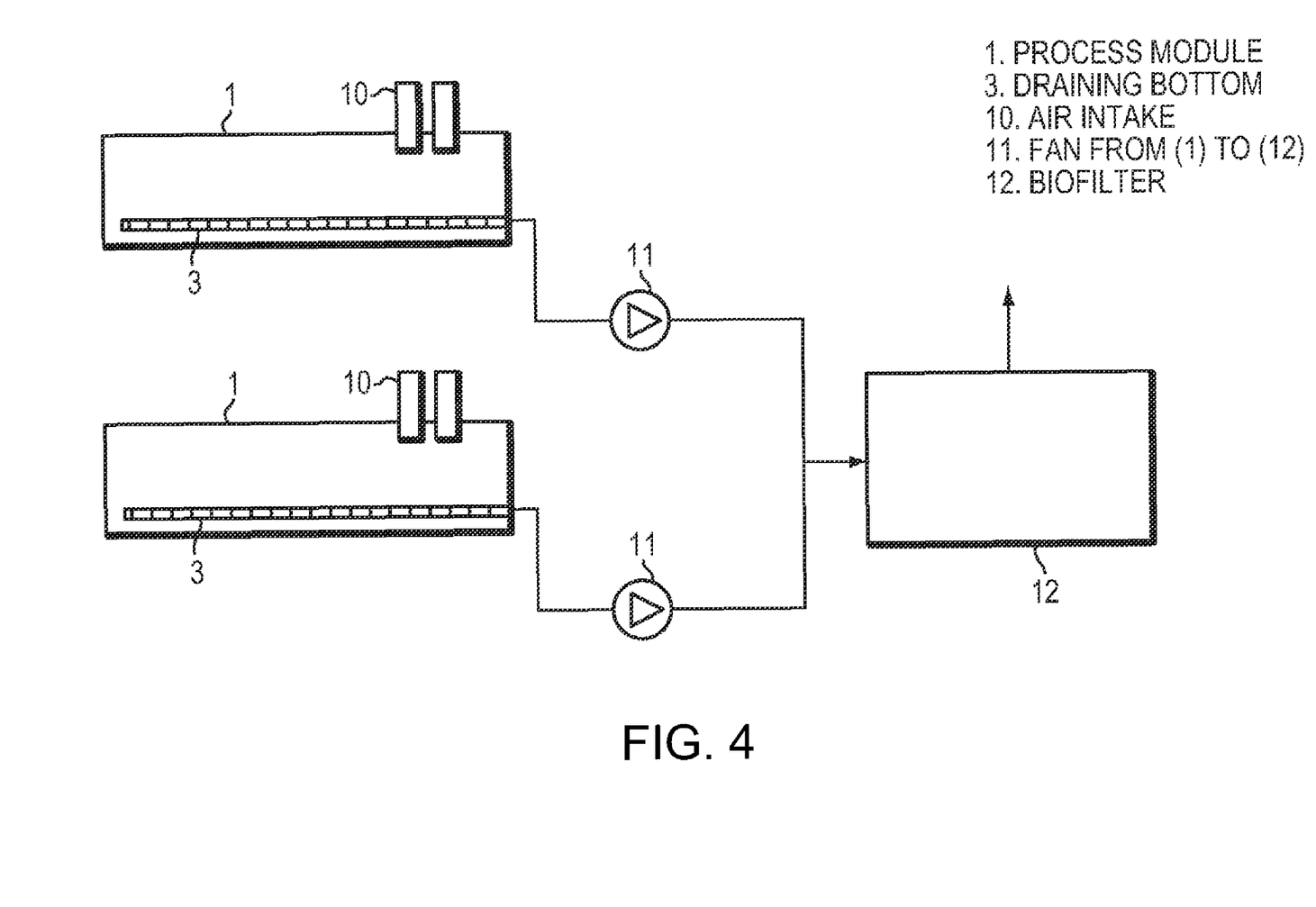
FIG. 4 is a schematic drawing of an apparatus for digestion and composting of solid waste, highlighting components involved in the composting stage, in accordance with an embodiment of the invention.

FIG. 3 and FIG. 4 are analogous to FIG. 1 and FIG. 2, respectively, with minor changes in the process streams during the hydrolysis/methanogenesis stages (methanization process) depicted in FIG. 3. In FIG. 3, percolate that passes through the drain 3 at the bottom of a process module 1 first passes through a filter tank 6 prior to entry into the process tank 5. The filter tanks 6 are equipped with a coarse filter where bigger pieces (e.g., large solids) can be separated from the liquid stream. Degassed percolation liquid from the biogas reactor tank 9 is also discharged to the process tanks 5, e.g., using pumps. Thus, the process tanks 5 collect percolate from the process modules 1 as well as liquid recycled from the biogas reactor tank 9, as depicted in FIG. 3. Liquid from a process tank 5 is pumped to a spraying system 2 in one or more process modules 1 (FIG. 3 depicts one process tank 5 per process module 1, but alternative embodiments may have multiple process modules 1 sharing a single process tank 5). The spraying system 2 continuously or discontinuously sprays the liquid over the organic matter in the process modules 1 by means of pumps 4. FIG. 3 depicts two process modules 1—each with associated process tank 5 and filter tank 6—for every biogas reactor tank 9. However, there may be many process modules 1 for a given biogas reactor tank 9. For example, in various embodiments, a plant may have at least 5, 10, 15, or 20 process modules 1 for a given biogas reactor tank 9.

After the hydrolysis and methanogenesis stage depicted in FIG. 3, the conditions in the process modules 1 shifts from anaerobic to aerobic, as air is introduced. FIG. 4 depicts this aerobic composting stage, where the same process modules 1 through which percolate flowed in the hydrolysis/methanogenesis stage are used for aerobic treatment of the organic waste, thereby obviating transport of the solids to another vessel. In the depicted embodiment, air intakes 10 mounted on top of the process modules 1, as shown in FIG. 4, are opened and pumps 11 start to draw air continuously or discontinuously (e.g., intermittently) through the already percolated organic matter. After passing through the organic matter, the air is discharged through a biofilter 12, where odors are scrubbed (e.g., using microorganisms) from the air.

Exemplary Embodiment

An example implementation of the system depicted in FIG. 3 and FIG. 3 is described in this section. In this example, the system produces biogas by anaerobic digestion of solid waste material (e.g., municipal waste) over a period lasting from one to four weeks. The de-gasified material is then decomposed through aerobic decomposition into a rich black soil, a process which takes an additional two to four weeks. The system allows control of the biological processes while avoiding over-engineering of the technical facilities.

The municipal waste is weighed and registered, after which it is unloaded in a reception area where the quality and pureness of the material is assessed. Surface fluid from the reception area is led through an oil separator and a sand collector to a receiving tank, then pumped to sewer.

The solid municipal waste is then handled and pre-treated using mobile equipment such as front loaders, feed mixers and drum screens. Non-organic components such as plastic, metal, and the like are separated out for incineration. The remaining waste is treated in a drum screen filter. The filtered-out fraction is transported to incineration while the 'clean' fraction is mixed with structure material such as wood branches and rough garden waste in a feed mixer. In this example, approximately 2 kg of structure material is used for every 10 kg of waste. The mixed material is front loaded into the process modules 1. When full, each module 1 is closed by bolting the gas tight door shut.

Biogas is produced in two phases—hydrolysis and methanogenesis. Hydrolysis takes place in the process modules 1, e.g., 600 $m^3$ concrete boxes or vessels, where each module 1 is fitted with sprinklers 2 and ventilations systems 10. The organic waste in the closed process module is irrigated with percolate from the process tank 5. This percolation draws out the fatty acids from the waste and the acidic percolate is then used for gas production in the reactor tank 9. The hydrolysis in the process module 1 runs for a period from two to four weeks.

Methane is produced in a gas tight reactor tank 9 (e.g., 1,500 $m^3$ membrane-covered concrete container), which is also used for gas storage. The fluids (percolate) from the hydrolysis in the process modules 1 are led to the reactor tank 9 where they feed the methanogenesis. Addition of percolate is controlled by the pH value in the reactor tank. The pH in the tank should be from about 7 to about 7.5 for good gas production. The process in the reactor tank 9 may take place without stirring, or with only light stirring. The reactor tank 9 design may simply be a modification of bio-gasification tanks used for livestock manure on farms.

The two processes—hydrolysis and methanogenesis—are thus handled in physically separate containers, and the interface between the two containers is a separate process tank 5 (e.g., a 6 $m^3$ vessel). Process control is performed in the process tank 5 and all related installations, including valves, pumps, fans, and the like, can be established in or around the process tank. This allows there to be no electrical installations in the process modules 1 or the reactor tank 9. In preferred embodiments, there is one process tank 5 connected to each process module 1. A plant that employs this system may have, for example, twenty process modules 1, each with a corresponding process tank 5, placed next to or opposite each other, and two reactor tanks 9, thus, in this example, 5 process modules 1 for every biogas reactor tank 9.

From the reactor tank 9, the biogas can be led to a biogas motor that produces electricity supplied to the electricity grid and heat which is used internally in the system. The internal heating system can transfer heat from the biogas motor to the reactor 9, offices, etc. Alternatively, the biogas can be captured and upgraded to higher methane content and fed to a natural gas system. A gas control unit measures gas flow and quality in the gas pipes, expressed by methane content, $CO_2$ content, and $O_2$ content. In addition to methane, $CO_2$ may be captured as well. The plant may be equipped with an emergency gas exploitation unit (e.g., gas flare) to exploit gas in the event of a biogas motor breakdown or during repair.

Once the hydrolysis is complete, pathogenic microorganisms are removed from the material in a sanitation step where the temperature in the process module is raised to a minimum of 70° C. and for a minimum of one hour. After purification, the waste in the process modules 1 can be converted to compost in the composting stage.

The composting process, depicted in FIG. 4, is activated by forced aeration of the now de-gasified waste, at which time composting begins and pH rises. The aeration may be performed by opening a pneumatic controlled damper 10 in the roof of the process module 1, thereby allowing atmospheric air into the module 1. Each process module 1 has its own air intake 10. The air is sucked out through the drainage bottom 3 via canals in the floor of the process module 1 using a fan placed outside the process module 1.

Composting will generally run for two to four weeks in the process module 1, after which the compost is stable and can be moved to open curing boxes for final composting without odor problems. The ventilation system transports air through the compost mass and sucks out process air to an air cleaning system 12. Process air cleaning is used to break down and clean odor components, such as ammonia. The air may be cleaned in a simple open surface biofilter or, if required, it can be wasted in a scrubber and subsequently cleaned in a biofilter. If the plant is equipped with a scrubber, then a water recycling system may be established to minimize water use.

Figure 5:
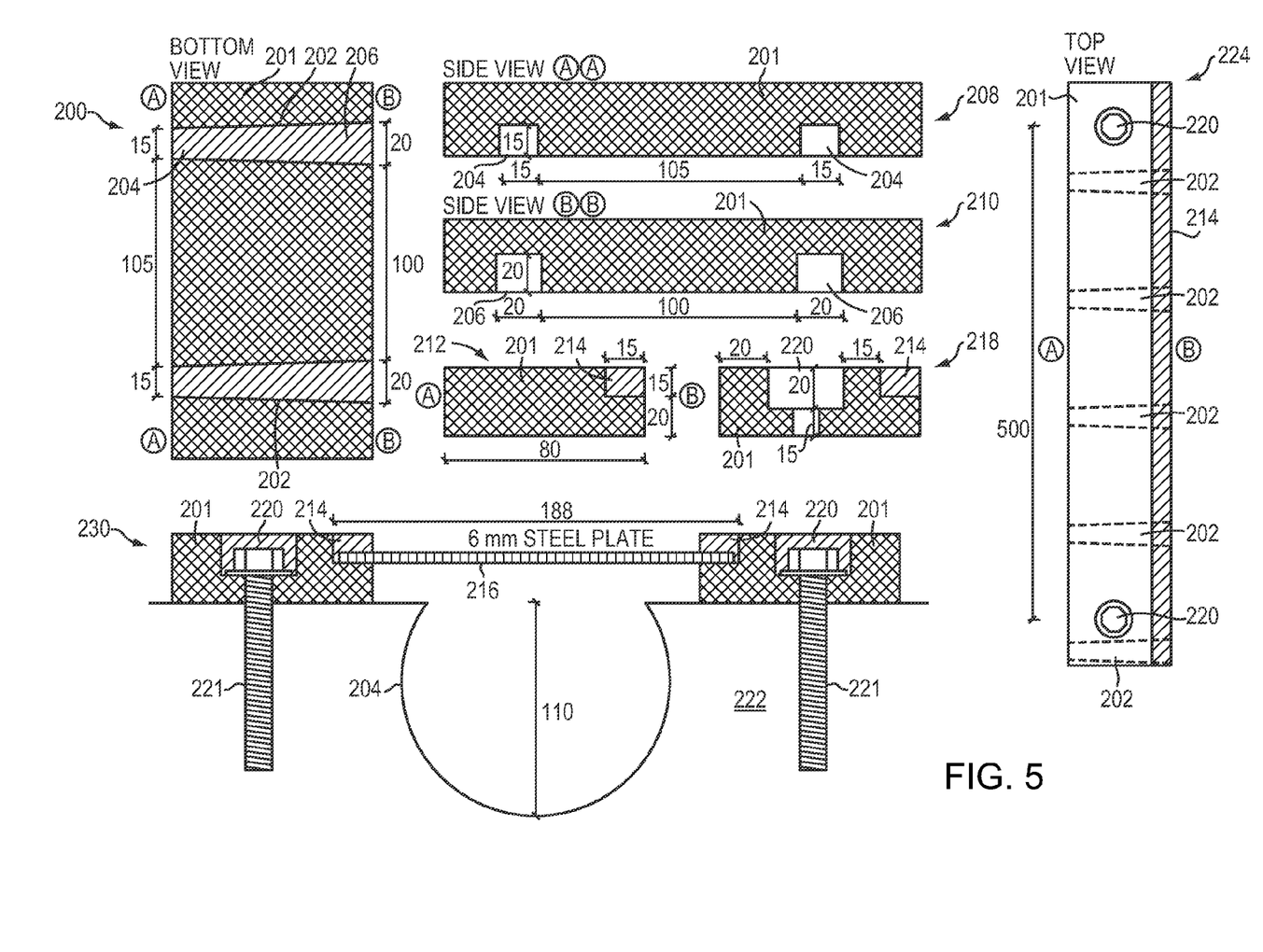
FIG. 5 is a schematic drawing of views of a dual-purpose drain assembly for transport of percolate from a process module during a digestion stage as well as for ventilation of the process module during a composting stage, in accordance with an embodiment of the invention.

FIG. 5 is a schematic drawing of views of an exemplary dual-purpose drain assembly 3 for transport of percolate from a process module 1 during a digestion stage as well as for ventilation of the process module 1 during a composting stage. The exemplary dimensions shown are in millimeters. Reference 200 is a bottom view of a rail 201, with funnels 202 through which percolate runs from the module (side A) to a pipe 204 (side B) during the digestion stage (hydrolysis/methanogenesis) and through which air flows from the pipe 204 (side B) to the module (side A). The funnels 202 have a conical shape, with the narrow end 204 facing the process module 1 and the wide end 206 facing the pipe 204. This design has been found to help prevent clogging of the funnel 202 with biomass in the process module 1. In certain embodiments, the ratio of the diameter at the narrow end 204 to the diameter at the wide end 206 is about 0.75. In certain embodiments, the ratio is no greater than about 0.90.

Reference 208 is a side view of a rail 201 from the process module 1 side (side A), showing the narrow end 204 of the funnels 202. Reference 210 is a side view of the rail 201 from the pipe side (side B), showing the wide end 206 of the funnels 202. Reference 212 is a ground view of the rail 201 showing pre-fabricated shelves 214 which hold a steel plate 216, and reference 218 is a ground view of the rail 201 showing pre-fabricated screw holes 220 for screws 221 that bolt the rail 201 to the concrete 222.

Reference 224 is a top view of the rail 201. This view shows the pre-fabricated screw holes 220 for the screws 221 that bolt the rail 201 to the concrete 222, and the prefabricated shelf 214 that holds the steel plate 216. Dotted lines represent the funnels 202 described above.

Reference 230 is a ground view of the drainage system. Rails 201 are on either side of a pipe 204. The rail may be made from polyethylene PEHD LF 1000, for example. Funnels 202 are drilled through the rails 201 to allow liquid percolate to flow from the process module 1 to the pipe 204 during the hydrolysis stage, and to allow flow of air from the pipe 204 to the process module 1 during the composting stage. A screw 221 bolts the rail 201 directly into the concrete 222.

Percolate flows from the process module 1 into the pipe 204, and from there is transported to the filter tank 6, process tank 5, and then biogas reactor tank 9 during the hydrolysis/methanogenesis stage. Furthermore, during the composting stage, air flows through the pipe 204 and into the process module 1 via the funnels 202. A steel plate 216 (e.g., 6 mm-thick stainless steel) tops the pipe 204 and compost lies on top of the steel plate 216. The steel plate 216 prevents compost/waste in the process module 1 from falling directly into the pipe 204. The plate 216 is held in place by a shelf 214 fabricated into the rails 201. The shelf 214 allows the plate 216 to be easily removed for cleaning of the pipe 204 when composting is complete and the solid material has been removed from the process module 1.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An apparatus for decomposition of organic matter into biogas and compost, the apparatus comprising:
    a waste processing tank into which solid organic waste is loaded and in which hydrolysis and composting takes place at separate times, with composting of the solid organic waste taking place during a separate stage after hydrolysis is completed, wherein the waste processing tank comprises a drain at or near its base, the drain allowing flow of percolation liquid out of the waste processing tank during the hydrolysis stage, the drain also serving as a vent through which air flows into and/or out of the solid organic waste in the waste processing tank during the composting stage;
    a spraying system configured to spray percolate liquid onto the solid organic waste in the waste processing tank during the hydrolysis stage, wherein the percolate liquid comprises fatty acids leached from the solid organic waste and wherein the percolate liquid is recycled from the base of the waste processing tank during the hydrolysis stage; and
    a biogas reactor tank into which the percolate liquid from the waste processing tank is pumped for generation of biogas under anaerobic conditions during a gasification stage,
    wherein the drain comprises a dual-purpose drain assembly for transport of the percolation liquid from the waste processing tank during the hydrolysis stage and for ventilation of the waste processing tank during the composting stage, the drain assembly comprising:
        a channel disposed below the processing tank;
        one or more rails through which a plurality of conduits are drilled, wherein each of the conduits has (i) a first end facing the waste processing tank containing the solid organic waste being processed and (ii) a second end facing the channel through which the percolation liquid flows out of the waste processing tank during the hydrolysis stage and through which air flows into the waste processing tank during the composting stage, wherein the first end has a width or diameter smaller than the second end; and
        a removable plate supported by the one or more rails, the plate covering the channel to prevent the solid organic waste in the waste processing tank from entering the channel.

2. The apparatus of claim 1, wherein the waste processing tank is configured to operate at ambient pressure during the hydrolysis stage, the composting stage, or both.

3. The apparatus of claim 1, wherein the waste processing tank is configured to operate under anaerobic conditions during the hydrolysis stage.

4. The apparatus of claim 1, further comprising a biofilter through which air from the waste processing tank passes prior to discharge to the atmosphere during the composting stage.

5. The apparatus of claim 1, further comprising a filter configured to separate solids from the percolate liquid.

6. The apparatus of claim 1, comprising at least two waste processing tanks connected in parallel.

7. The apparatus of claim 1, wherein the waste processing tank comprises an acid-resistant lining or coating.

8. The apparatus of claim 1, wherein the biogas reactor tank is gas-tight.

9. The apparatus of claim 1, further comprising a heater for heating the percolate liquid either in the biogas reactor tank or outside the biogas reactor tank.

10. The apparatus of claim 1, wherein the biogas reactor tank comprises a sump to separate sediment and/or particles from the percolate liquid.

11. The apparatus of claim 1, further comprising a liquid process tank into which percolate liquid from either the biogas reactor tank, the waste processing tank, or both flows prior to being pumped to the spraying system for spraying onto the solid organic waste in the waste processing tank during the hydrolysis stage.

12. The apparatus of claim 11, wherein percolate liquid from both the biogas reactor tank and the waste processing tank flows into the liquid process tank prior to being pumped to the spraying system for spraying onto the solid organic waste in the waste processing tank during the hydrolysis stage.

13. The apparatus of claim 12, further comprising a filter tank configured to separate solids from the percolate liquid before the percolate liquid enters the liquid process tank.

14. The apparatus of claim 11, comprising one liquid process tank for each waste processing tank.

15. The apparatus of claim 14, comprising at least five waste processing tanks for each of one or more biogas reactor tanks.

16. The apparatus of claim 1, wherein the first end has a diameter no greater than 90% of the diameter of the second end.

17. The apparatus of claim 1, wherein each of the one or more rails comprises a notch, thereby forming a shelf for supporting the removable plate.

18. The apparatus of claim 1, wherein the channel is formed in a concrete base below the waste processing tank.

19. The apparatus of claim 1, comprising two or more rails, wherein the two or more rails comprises at least a first rail disposed along a first edge of the channel and a second rail disposed along a second edge of the channel.

20. The apparatus of claim 1, wherein at least a portion of the percolate liquid sprayed onto the solid organic waste in the waste processing tank during the hydrolysis stage is received from the base of the waste processing tank without first passing through the biogas reactor tank.

* * * * *